United States Patent
Bindell et al.

(10) Patent No.: US 6,297,503 B1
(45) Date of Patent: Oct. 2, 2001

(54) METHOD OF DETECTING SEMICONDUCTOR DEFECTS

(75) Inventors: Jeffrey B. Bindell; Frederick A. Stevie, both of Orlando, FL (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/328,560

(22) Filed: Jun. 9, 1999

(51) Int. Cl.⁷ .......... H01L 21/44; H01L 21/302; H01J 37/317
(52) U.S. Cl. .......... 250/307; 250/306; 250/492.2; 250/492.21; 250/493.1; 438/473
(58) Field of Search ................ 250/307, 306, 250/492.2, 492.21, 493.1; 438/473

(56) References Cited

U.S. PATENT DOCUMENTS

| | | | |
|---|---|---|---|
| 5,236,547 | 8/1993 | Takahashi et al. | 156/628 |
| 5,270,552 | 12/1993 | Ohnishi et al. | 250/307 |
| 5,306,663 | 4/1994 | Morimoto | 437/173 |
| 5,429,994 | * 7/1995 | Ishikawa | 437/230 |
| 5,482,802 | 1/1996 | Celler et al. | 430/5 |
| 5,504,340 | 4/1996 | Mizumura et al. | 250/492.21 |
| 5,523,694 | 6/1996 | Cole, Jr. | 324/751 |
| 5,583,344 | 12/1996 | Mizumura et al. | 250/492.21 |
| 5,650,337 | 7/1997 | Cahen et al. | 437/16 |
| 5,761,064 | 6/1998 | La et al. | 364/468.17 |
| 5,804,980 | 9/1998 | Nikawa | 324/752 |
| 5,838,005 | 11/1998 | Majumdar et al. | 250/306 |
| 5,877,519 | 3/1999 | Jewell | 257/190 |
| 6,211,527 | * 4/2001 | Chandler | 250/492.2 |

* cited by examiner

*Primary Examiner*—Bruce Anderson
*Assistant Examiner*—Nikita Wells
(74) *Attorney, Agent, or Firm*—Allen, Dyer, Doppelt, Milbrath & Gilchrist, P.A.

(57) ABSTRACT

A method of detecting defects within a semiconductor device is disclosed. An ion beam is focused in predetermined directions onto an area of a semiconductor device that is believed to have a suspected defect. A portion of the semiconductor device is milled and forms a thin film specimen to be removed from the semiconductor device. The thin film specimen is removed from the semiconductor device and placed onto an insulated film mount. Electrical connection points are created on previously unexposed portions of the thin film specimen by depositing a line of conductive material using a focused ion beam. The surface of the thin film specimen is scanned with an electron beam in a scanning electron microscope and observed for contrast. Processing errors are determined and the lateral resolution is about the electron beam size.

22 Claims, 7 Drawing Sheets

METHOD OF DETECTING SEMICONDUCTOR DEFECTS

FIELD OF THE INVENTION

This invention relates to the field of semiconductor device manufacturing, and more particularly, this invention relates to the field of detecting defects within a semiconductor device.

BACKGROUND OF THE INVENTION

Electron beam induced contrast (EBIC) is used in quality control of semiconductor device manufacturing because it allows a visual indication of defects in the semiconductor device. The EBIC process is used with a scanning electron microscope (SEM) to observe the semiconductor device and determine errors or quality defects in a specific transistor or junction. EBIC is a well-known non-destructive testing method for semiconductor devices.

Failure analysis methods are essential to determine defects in semiconductor devices. These processes can provide insight to different manufacturing and processing defects and failure modes that have to be corrected. EBIC is used in conjunction with an SEM to provide a focused electron beam and a method for scanning the electron beam over a portion of a semiconductor device, and typically an integrated circuit. The SEM also permits viewing of an image from the semiconductor device by using the secondary electron emission. The EBIC method is used to identify certain types of defects in a semiconductor device by measuring the electron-hole current induced in a semiconductor junction of an integrated circuit by an impinging beam of electrons. One drawback of the EBIC technique is the impinging electrons penetrate a significant distance into the device and also physically spread out into a larger volume in this process. The result of this is that the spatial resolution is substantially reduced making small defects impossible to detect. The primary electron beam must have adequate energy to penetrate through passivation layers to reach the active semiconductor device layer in the integrated circuit having the possible defect. This process also leads to spreading of the beam's effective size.

The EBIC (electron beam induced current) process records the variation of electron hole recombination rates with position by measuring the electrical currents created by the impinging electron beam in local portions of a semiconductor device. These defects include dislocations and defects in the grain boundaries. Electron beams are often used in preference to a laser, e.g., a light beam induced current (LBIC), because the electron beam allows a finer resolution and can create more electron hole pairs. In an EBIC process, the electron beam is scanned perpendicular to the surface of the semiconductor device and the electrons create large numbers of electron-hole pairs within or near to the depletion regions of the semiconductor device. The electrical charges so produced can be collected by the semiconductor device p-n junction induced currents. If the scan includes a grain boundary or other defect, a fraction of the carriers can recombine at different rates, thereby changing the local current generation. Parameters that characterize the defect can be extracted from EBIC line scans, including recombination velocity, $V_s$, and minority-carrier diffusion length.

Because of the resolution limitations mentioned above, the EBIC method is commonly used on large semiconductor devices. However, the method does not adequately provide a determination of an exact location of a defect.

SUMMARY OF THE INVENTION

It is therefore an object of the present invention to provide a method of detecting defects within a semiconductor device that allows the detection of defects with more exact certainty than a standard EBIC process.

In accordance with the present invention, a method of detecting defects within a semiconductor device includes the steps of focusing an ion beam in predetermined directions onto an area of a semiconductor device that is believed to have a suspected defect. A portion of the semiconductor device is then milled with the ion beam to form a thin film specimen that is to be removed from the semiconductor device. The thin film specimen is removed from the semiconductor device and placed onto an insulated film mount. Electrical connection points are created on typically what were previously unexposed portions of the thin film specimen by depositing a line of conductive material using a focused ion beam. The surface of the thin film specimen is then scanned with an electron beam in a scanning electron microscope. Internally generated currents as detected by a suitable external amplifier are analyzed. Processing errors of the thin film specimen are then determined and lateral resolution is about the electron beam size.

The focused ion beam allows milling of the semiconductor device such that the thin film specimen has typical dimensions of thickness about 0.1 micrometers, a length of about 20 micrometers, and a width of about 5 micrometers.

In still another aspect of the present invention, the method comprises the steps of depositing a conductive material using a gallium or other appropriate ion emitted from the focused ion beam. The electrical connection points can be created by irradiating gallium or other appropriate ions onto predetermined sections of the thin film specimen by the focused ion beam. A conductive film is then deposited onto the irradiated sections using the focused ion beam to create the electrical connection points. The thin film specimen can be mounted onto a holder, such as a transmission electron microscope grid, before creating the electrical connection points. The method can also include the step of removing the thin film specimen by a charged glass removal tool or metal tip with applied voltage.

BRIEF DESCRIPTION OF THE DRAWINGS

Other objects, features and advantages of the present invention will become apparent from the detailed description of the invention which follows, when considered in light of the accompanying drawings in which.

DETAILED DESCRIPTION OF THE PREFERRED EMBODIMENTS

Figure 1A:
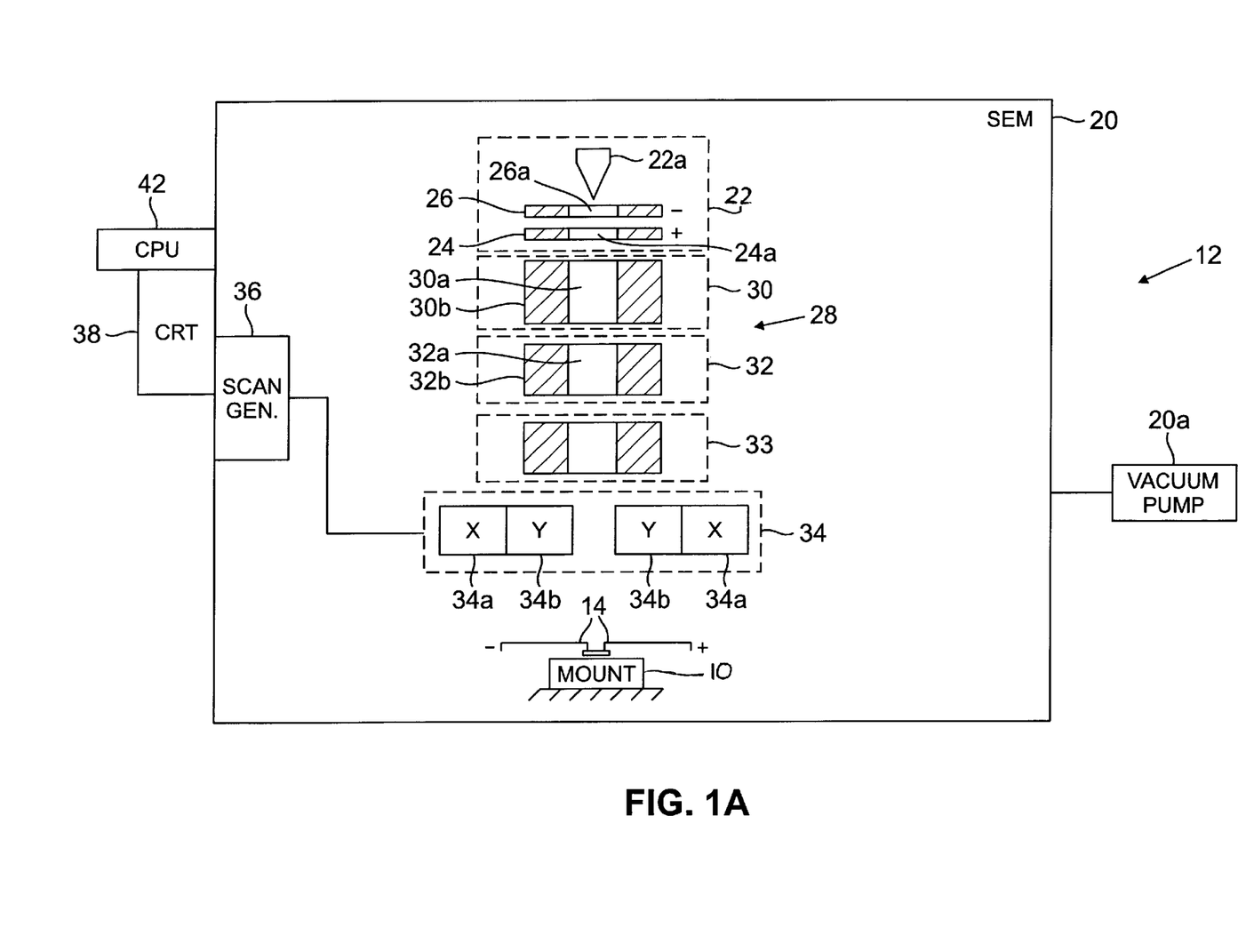
FIG. 1A is a schematic diagram of a scanning electron microscope and a mount that holds a sample to be exposed to the electron beam to form a secondary electron image as a charge is sent across the semiconductor device such that the induced voltage affects the electron beam.
Figure 1B:
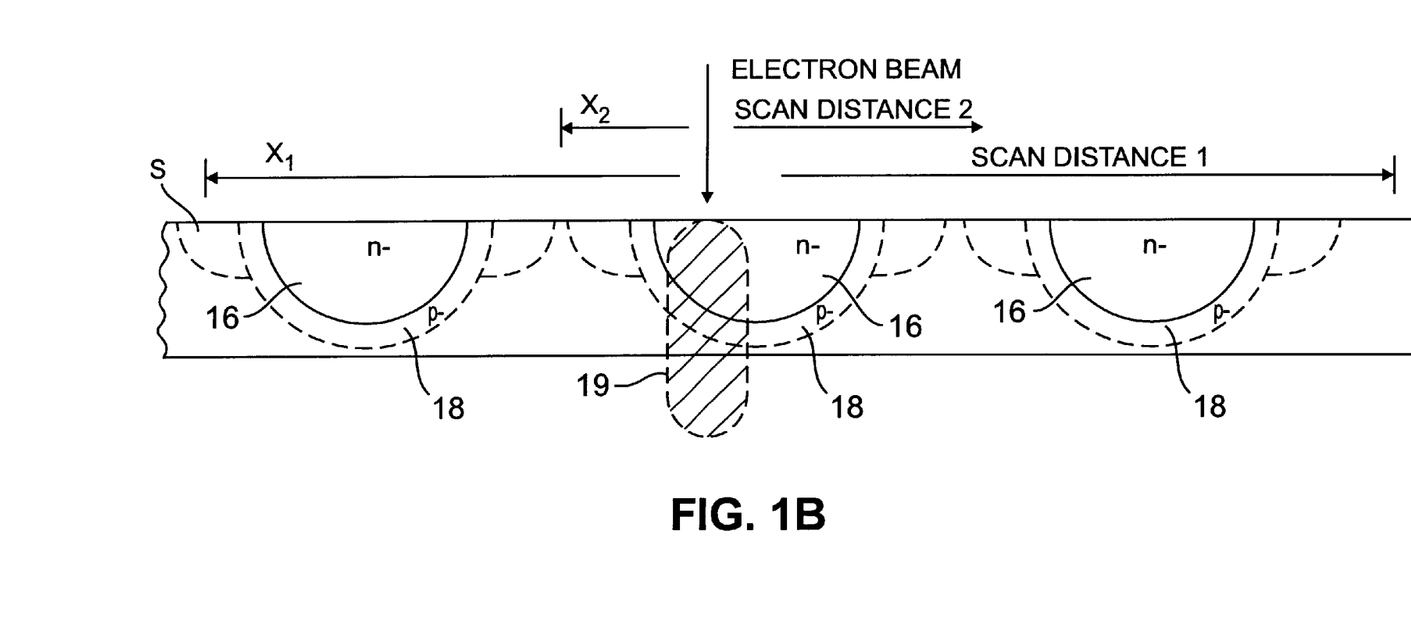
FIG. 1B is an enlarged section of a semiconductor device showing a prior art technique of EBIC analysis.

Referring now to FIG. 1A, there is illustrated a large semiconductor device(s) mounted on a support mount 10 of a scanning electron microscope (SEM) 12. An electrical current is placed through the semiconductor devices via electrical connection points 14 to induce an electron beam induced contrast. The semiconductor device is then scanned with the scanning electron microscope 12, such that the voltage and charge across the semiconductor device affect the electron beam and forms a secondary electron image. FIG. 1B illustrates a known technique of electron beam induced contrast. For purposes of illustration and clarity, the details of the scanning electron microscope are described with reference to FIG. 1A.

The semiconductor device S to be scanned is typically multilayered and has various depths of different devices contained in the semiconductor device. A portion of a larger semiconductor device is shown in FIG. 1B. The semiconductor device includes an n doped region 16 and a p doped region 18. Although not illustrated in detail, the semiconductor device typically has many layers and devices of different layers. The scanned distance across the semiconductor device can vary depending on what portion is scanned. Two scanned distances are illustrated $X_1$ and $X_2$. The larger distance $X_1$ could be an initial scan, and shorter distance $X_2$ would be used to ascertain a better determination of defects in a selected portion of the semiconductor devices. As illustrated, a generation volume 19 in the form of an oval is created in the semiconductor device. The signal emanates from the generator volume.

The scanning electron microscope 12 has advantages over optical microscopy because of inherent limitations in an optical microscope, such as the short focal length of the high power objective lens, an increased aperture angle and decreased depth of field. Electrons used in a scanning electron microscope, on the other hand, have a smaller wavelength than visible light, and thus, the potential for a much higher resolution exists. The SEM 12 has a long working distance (distance between the sample and final lense) and a small aperture opening, thus making a shallow aperture angle and good depth of field.

The SEM 12 will be described with reference to FIG. 1A, where one technical example of a SEM is illustrated. Other types of SEM known to those skilled in the art can be used. The electron source, lenses and sample or specimen are contained in a large vacuum chamber 20 because electrons cannot travel freely through air. The vacuum chamber 20 can act as the housing of the SEM. A vacuum pump 20a draws air from the chamber 20. Because electrons are electrically charged, the sample to be scanned must be conductive enough to dissipate the charge.

In a SEM 12, electrons from source 22 are focused on the sample. The SEM 12 includes an electron gun 22 having a hot cathode source 22a, typically a tungsten filament. The filament is heated and the current is passed through the filament, emitting light. An electron cloud forms around the filament.

A positively charged plate (an anode) 24 is placed near the filament. The electrons are negatively charged and will be attracted to it. The electrons would probably jump over to the anode plate in a series of arcs, but a negatively charged cathode plate 26 is placed near the filament (thus being repelled by the cathode). The electron cloud is attracted to the anode plate 24 such that the electrons travel through the hole 26a in the cathode plate 26 and gain enough speed such that most of them travel through the hole 24a in the anode plate 24. The speed of electrons emitted from this electron gun 22 can be controlled by the accelerating voltage of the potential applied to the cathode and anode plates 24,26, as is well known to those skilled in the art.

The electrons are emitted from the electron gun 22 in a spray pattern and require various means, such as electromagnetic lenses to control the flow of electrons. By varying the current through a lens, a lens can have a variable focal length.

The SEM 12 typically is formed as a SEM column 28 where the electron gun 22 and lenses are mounted in the vacuum chamber 20.

The condensor lens 30 controls the size of the beam and the amount of electrons traveling down the SEM column 28. The lens 30 includes a solid portion 30b and cylindrical core 30a through which electrons pass. By increasing the size of the beam, a better signal to noise ratio can be achieved. When the beam diameter is larger, it gives a lower resolution. Depending on the magnification, a compromise between the signal to noise and resolution achieves the best image quality. An objective lens 32 focuses the beam into one spot on a sample to be examined, and includes the core 32a and solid portion 32b. Another lens 33 could be included for fine tuning, as known to those skilled in the art.

Although the electron beam can now be focused into a direct spot on the sample, the fixed beam would damage or contaminate the device at that spot. It must be scanned. The scan coils 34 include x and y plates 34a, 34b, which are placed around the beam and vary the potential between them. Thus, the electron beam is deflected. These scan coils are attached to a scan generator 36 that allows the beam to scan lines across the sample. The scan generator 36 is also connected to a CRT 38. The scan generator 36 controls the beam of the CRT 38 such that a secondary electron image can be formed on the CRT and synchronized to the electron beam that scans the sample.

As is well known to those skilled in the art, as an electron beam scans across a sample, the beam is synchronized to the beam of the CRT. The incident beam electrons from the electron gun 22 travel through a sample and can pass through the sample without colliding with any sample electrons. The beam electrons can also collide with sample electrons, creating secondary electrons, or collide with the nucleus of the sample atom, creating a back scattered electron. This incident electron beam is composed of energized electrons. If one of the electrons collides with the sample atom electron, it knocks the sample atom electron out of the shell and this electron becomes a secondary electron that is reduced in energy (near 100 volts). If the secondary electrons are close enough to the sample surface, they are collected to form a secondary electron image. If any incident beam collides with a nucleus of a sample atom, it bounces back out of the sample as a back scattered electron. These electrons have high energies and because a sample with higher density could create a greater number of back scattered electrons than a sample with lower density, these electrons can be used to form a back scattered electron image to discern differences in sample densities.

In FIG. 1A, a charge is sent throughout the semiconductor device via a series of electrical connection points 14. An electron beam from the scanning electron microscope is scanned across a distance X. The CRT 38 in FIG. 1A forms a secondary electron image of the detected charge and emitted light. A second distance $X_2$, which is shorter, could be used to define a more exact scan for a defect. However, as noted before, the standard EBIC method has drawbacks because it does not adequately determine defects, especially with the emergence of numerous semiconductor devices having numerous different layers and p-n junctions at different depths throughout a semiconductor device. The method of the present invention solves this problem.

Figure 2A:
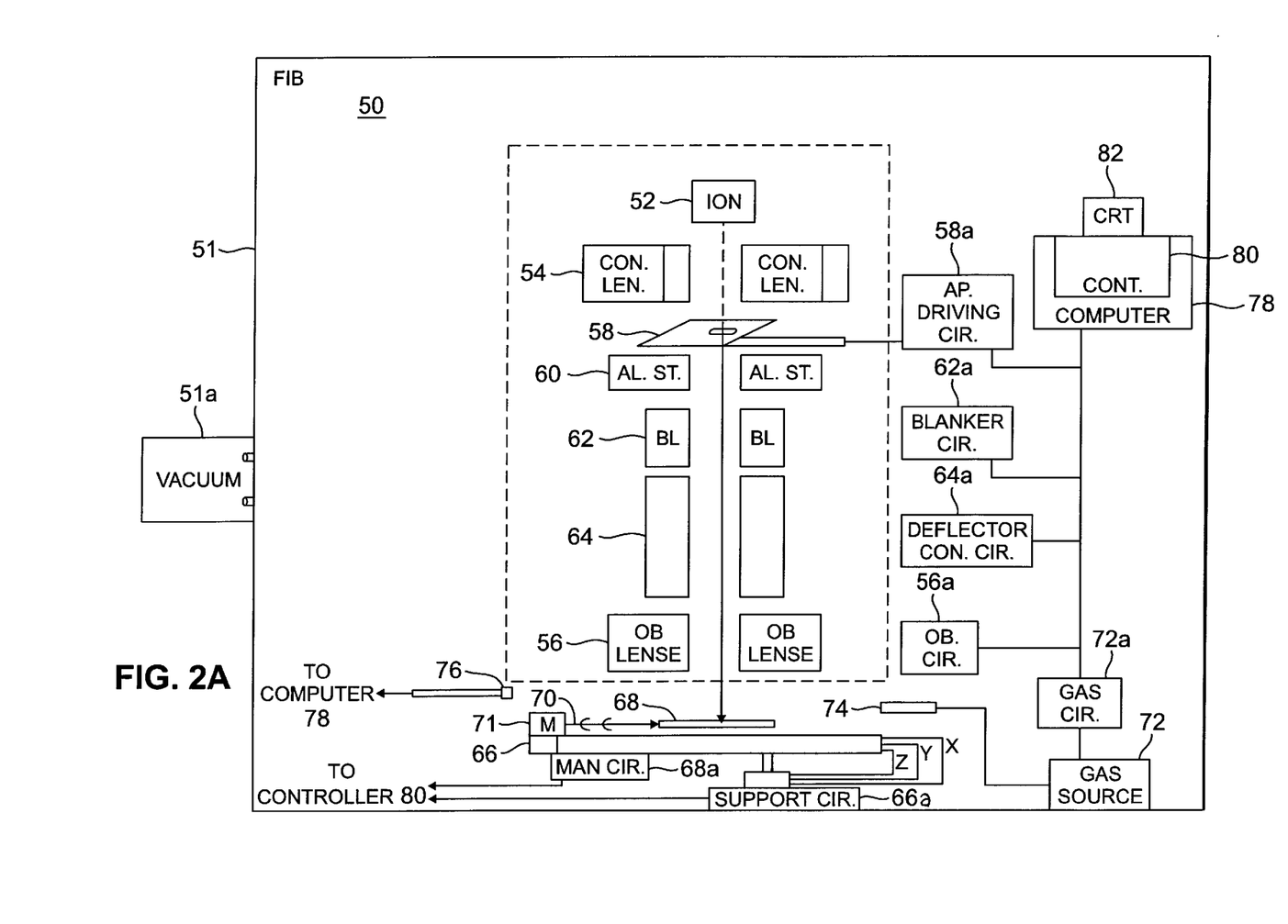
FIG. 2A is a schematic diagram of a focused ion beam (FIB) device and shows its use in milling a semiconductor device for forming a thin film specimen.
Figure 3:
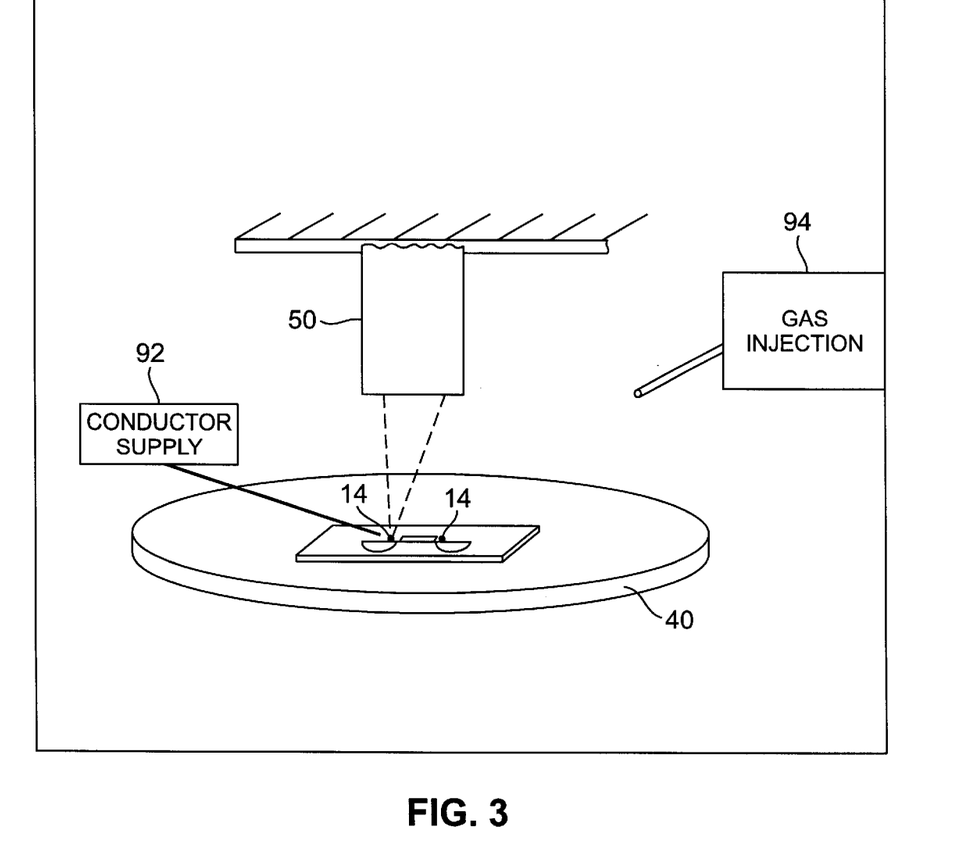
FIG. 3 shows a thin film specimen of the present invention mounted on an insulated film mount where electrical connection points are created on the thin film mount.
Figure 4:
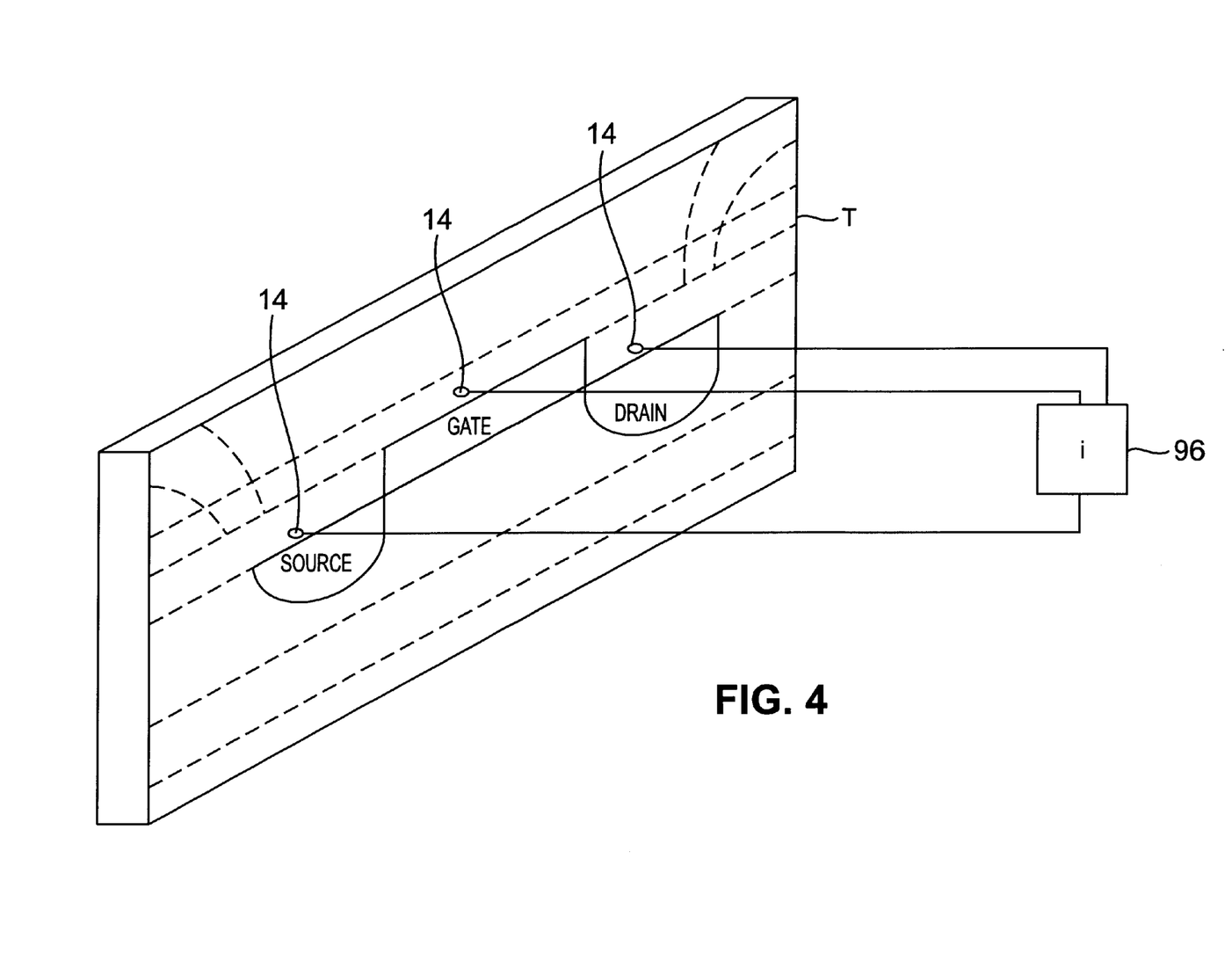
FIG. 4 is a schematic diagram showing the surface of the thin film specimen being scanned to determine processing errors.

In accordance with the present invention, a focused ion beam (I) is generated in predetermined directions onto an area of the semiconductor device that is believed to have a suspected defect (FIG. 2A). A portion of the semiconductor devices is milled by the focused ion beam to form a thin film specimen (T), which is later removed from the semiconductor device. This thin film specimen (T) is then removed and placed onto an insulated film mount 40 (FIG. 3) where electrical connection points 14 are created on portions of the thin film specimen by depositing a line of conductive material using a focused ion beam (FIG. 3). Typically, the electrical connection points are created on previously unexposed portions of the thin film specimen T. The sample is then removed and placed in the SEM 12. Current is generated through the electrical connection points 14. The surface of the thin film specimen is scanned with the electron beam in a scanning electron microscope (SEM) 12 (FIG. 4). Internally generated currents are detected by a suitable external amplifier, which could be part of the CPU 42. Processing errors are determined via appropriate algorithms in the controller and CPU 42 and lateral resolution is approximately the electron beam size (FIG. 1A).

For purposes of explanation, greater details are now described of the illustrated focused ion beam device, and other aspects of the present invention. Although only one type of focused ion beam device is illustrated, it should be understood that different types of focused ion beam devices can be used as known to those skilled in the art.

As shown in FIG. 2A, a focused ion beam device 50 (FIB) is illustrated. The FIB device 50 and associated components and peripherals, such as mounts, are contained in a large FIB vacuum chamber 51, where vacuum is drawn by vacuum pump 51*a*. A focused ion beam spot size can vary from micrometers to as finite as 5 nanometers, or 50 angstroms. The FIB device 50 can make precise drills and cuts (e.g., milling cuts).

The focused ion beam device 50 typically includes a liquid metal ion source 52 from which ions can be emitted. In one aspect of the present invention, gallium ions or other suitable ions known to those skilled in the art are emitted. The ion beam is focused on a specimen through a condenser lens 54 and a spaced objective lens 56. A selectable aperture 58 is positioned under the condenser lens 54 and liquid metal ion source 52. An aligner-stigmator 60, blanker 62 and deflector 64 can be arranged between the two lenses. The selectable aperture 58 is connected to an aperture driving circuit 58*a*. The blanker 62 is connected to a blanking amplifier circuit 62*a*. The deflector 64 can be connected to a deflection control circuit 64*a*. These types of circuits are known to those skilled in the art.

A support 66 on which semiconductor devices or other sample can be positioned is mounted for movement in at least three axes (x, y and z) directions, and often by appropriate control through various other axes. A specimen or other semiconductor device to be treated is mounted on a specimen manipulator 68 fixed to a rotary shaft 70 and driven by motor 71 mounted on the support 66. The specimen manipulator 68 allows movement in directions other than the x, y and z axis. A gas such as $WCO_6$ can be produced from a gas source 72 and inserted by nozzle 74 into the area where the semiconductor device is to be irradiated. The gas nozzle 74 can be positioned adjacent the semiconductor device that is positioned on the support 66.

Additionally, the FIB device 50 could include a secondary electron detector 76 that allows secondary electrons produced from the surface of the semiconductor device to be detected. The generated signal could be converted from an analog signal into a digital signal and supplied to a computer 78 that works in synchronism with the controller 80 that controls the deflection of the focused ion beam. Thus, an image can be formed by a scanning ion microscope and displayed on a cathode ray tube (CRT) 82.

The manipulator 68 is controlled by a manipulator control circuit 68*a* to allow manipulation in rotative directions as compared to the axes (x, y and z) controlled by a support circuit 66*a*. The controller 80 can control the aperture driving circuit 58*a* through a system bus 84 and select desired aperture from the selectable aperture 58. The computer 78 and associated controller 80 control the deflection control circuit 64, manipulator control circuit 68*a*, the support control circuit 66*a*, the gas source control circuit 72*a* and other circuits. All portions of the device 50 can be controlled, including the power source 56 for the lenses. These components are mounted in the vacuum chamber 51 to allow a gas free environment.

A second focused ion beam device 50' could also be mounted within the chamber 51 to allow a focused ion beam to be emitted at a different direction. However, typically, only one focused ion beam device is required. Any semiconductor device or sample is moved and rotated as necessary.

Figure 2B:
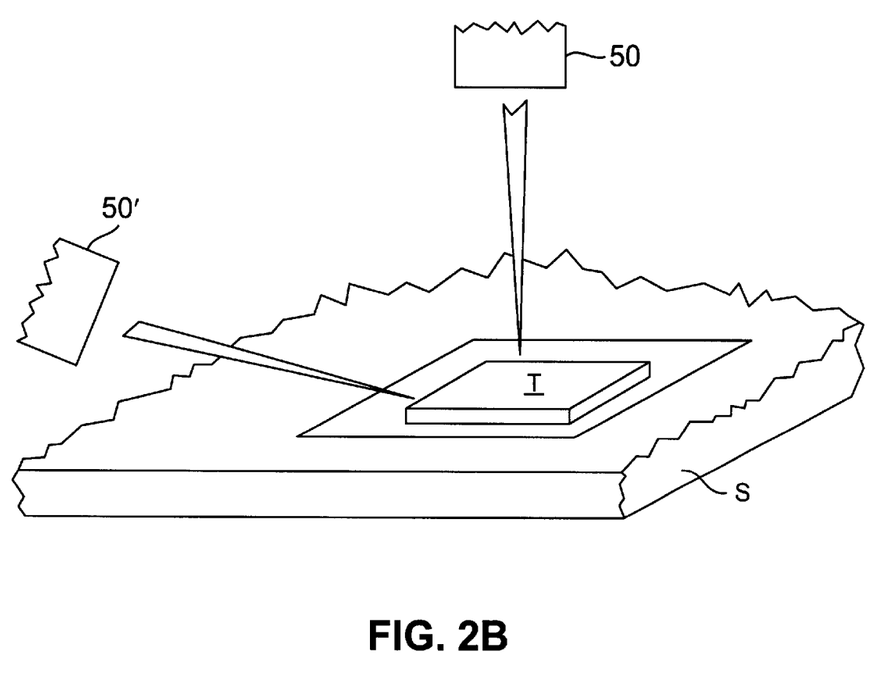
FIG. 2B is an enlarged perspective view of a portion of a semiconductor device that is being milled by a focused ion beam device.

As illustrated in FIG. 2B, a selected portion of the semiconductor device that is believed to have a defect is milled by the focused ion beam in a manner known to those skilled in the art to form a thin film specimen T to be later removed from the semiconductor device. The semiconductor device can be turned and rotated by the manipulator 68 on the support 66 to allow milling on the side and underneath between the specimen T and the semiconductor device T. In a process typically done outside the FIB, a charged glass removal tool (or possibly a metal tip with applied voltage), as known to those skilled in the art, is driven accurately over the semiconductor device and lowered onto the milled out thin film specimen T. The thin film specimen is then removed. The charged glass removal tool is charged adequately using static electricity to remove the thin film specimen. Typically, the focused ion beam mills the semiconductor device so that the thin film specimen T has a thickness of about 0.1 micrometers, a length of about 20 micrometers, and a width of about 5 micrometers. Naturally, not only are the sides of the thin film specimen milled by milling into the semiconductor device, but also the area underneath the thin film specimen is milled by manipulating the semiconductor device. In rare machines, a second FIB device could be used for such purposes, shown in FIG. 2B.

It is possible at this point, while the thin film specimen has not been removed from the semiconductor device, to create electrical connection points 14 in FIG. 3 on the thin film specimen. However, in a preferred aspect, the electrical connection points 14 are created on previously unexposed portions of the thin film specimen. Thus, the glass removal tool removes the thin film specimen and mounts it on an insulated film mount 40, such as a transmission electron microscope grid (FIG. 3). This type of grid typically has a 3 millimeter grid structure. Although a transmission electron microscope grid is used in this described embodiment, other insulated supports can be used as suggested and known to those skilled in the art.

At this time, the insulated film mount 40 is placed back into the FIB chamber 51 or another FIB device chamber. The focused ion beam is used to irradiate gallium or similar ions onto predetermined sections of the thin film specimen and deposit a conductive film onto irradiated sections using the focused ion beam by techniques known to those skilled in the art. In FIG. 3, a supply of conductor material 14 is used to apply the conductor material, or alternately, gas injected by gas injection source 94 can react with the areas that have been exposed to the ions from FIB 50 to create the electrical connection points 14. Typically, the unexposed portions of the thin film specimen will have electrical connection points 14 formed thereon. The electrical connection points 14 can be positioned to allow current flow and induce the necessary contrast, which will induce the charges to the electrons to be determined by the scanning electron microscope. Only the device cut by FIB is ruined. Adjacent devices on a wafer could be used for later processing and applications.

As shown in FIG. 4, electrical connection points 14 are secured to a source of current 96. The current generates the light emissions that are detected by the electron beam emitted from the scanning electron microscope, and the secondary electron image formed as described before. The lateral resolution can be about the electron beam size because of the small thin film specimen that has been formed, using the focused ion beam device. Internally generated currents can be detected by a suitable external amplifier and processing errors can be determined. Thus, more exact certainty can be obtained with the scanning electron microscope through the use of the thin film specimen.

Figure 5A:
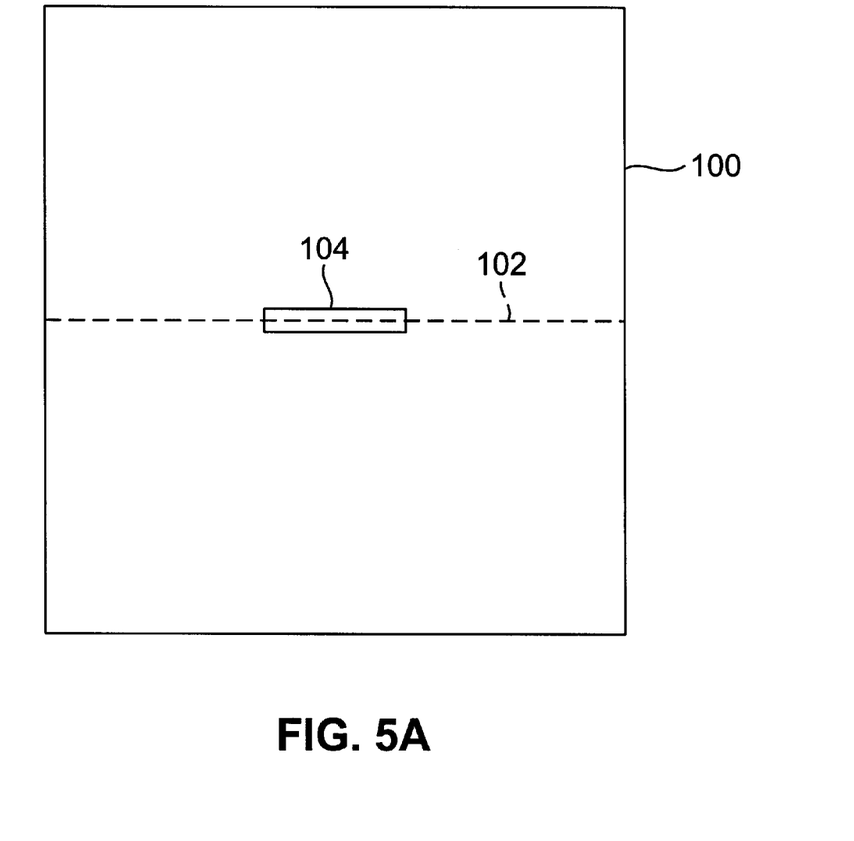
FIG. 5A shows a large part of a silicon sample with an area of interest with the dashed line indicating where the FIB makes a cut.
Figure 5B:
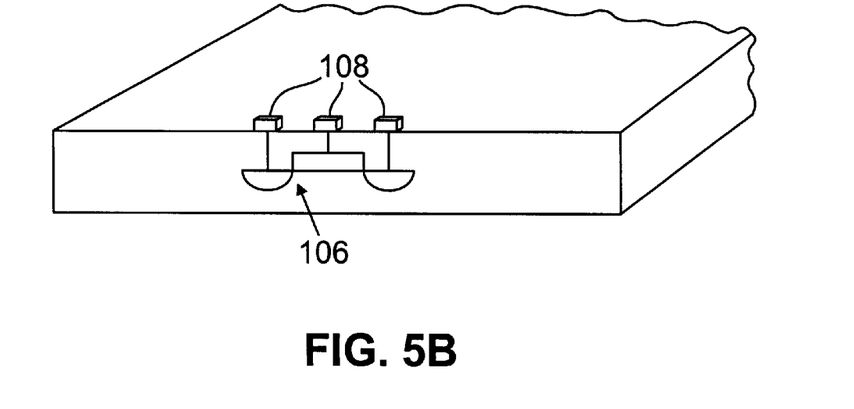
FIG. 5B shows the cut wafer with edge connections.

FIGS. 5A and 5B illustrate another embodiment where defects can be detected within a semiconductor device. A semiconductor device that is believed to have a suspected defect is shown at 100 and a cut line is shown at 102 through which a focused ion beam cuts the area of the semiconductor device to expose an area of interest 104 that is being analyzed for defects. FIG. 5B illustrates the area that is being cut with the focused ion beam and typically cleaved and polished. Electrical connection points are created to the edge of the wafer by depositing conductive material using a focused ion beam. The semiconductor device 106 is illustrated in FIG. 5B. The surface of the exposed area of interest is scanned with the electron beam in the scanning electron microscope and internally generated current, as detected by an external amplifier, are analyzed. Processing errors which can be identified in the wafer are then determined, wherein lateral resolution is about the electron beam size.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A method of detecting defects within a semiconductor device comprising the steps of:

focusing an ion beam in predetermined directions onto an area of a semiconductor device that is believed to have a suspected defect;

milling a portion of the semiconductor device and forming a thin film specimen to be removed from the semiconductor device;

removing the thin film specimen from the semiconductor device;

placing the thin film specimen onto an insulated film mount;

creating electrical connection points on previously unexposed portions of the thin film specimen by depositing a line of conductive material using a focused ion beam; and scanning the surface of the thin film specimen with an electron beam in a scanning electron microscope and analyzing internally generated currents as detected by a suitable external amplifier; and determining processing errors which can be identified in the thin film specimen, wherein lateral resolution is about the electron beam size.

2. A method according to claim 1, and further comprising the steps of milling the semiconductor device with the focused ion beam such that the thin film specimen has a thickness of about 0.1 micrometers.

3. A method according to claim 1, and further comprising the steps of milling the semiconductor device with the focused ion beam such that the thin film specimen has a length of about 20 micrometers and a width of about 5 micrometers.

4. A method according to claim 1, and further comprising the steps of depositing a conductive material using a gallium or other appropriate ion emitted from the focused ion beam.

5. A method according to claim 1, wherein the step of creating the electrical connection points further comprises the steps of:

irradiating gallium or other appropriate ions onto predetermined sections of the thin film specimen by a focused ion beam; and depositing a conductive film onto the irradiated sections using the focused ion beam to create the electrical connection points.

6. A method according to claim 1, and further comprising the step of mounting the thin film specimen onto a holder such as a transmission electron microscope grid before creating the electrical connection points.

7. A method according to claim 1, and further comprising the step of removing the thin film specimen by one of a charged glass removal tool or metal tip with applied voltage.

8. A method of detecting defects within a semiconductor device comprising the steps of:

focusing an ion beam in predetermined directions onto an area of a semiconductor device that is believed to have a suspected defect;

milling a portion of the semiconductor device and form a thin film specimen to be removed from the semiconductor device;

removing the thin film specimen from the semiconductor device;

creating electrical connection points on the thin film specimen by depositing a line of conductive material after removing the thin film specimen from the semiconductor device;

scanning the surface of the thin film specimen with an electron beam in a scanning electron microscope and analyzing internally generated currents as detected by a suitable external amplifier; and determining processing errors which can be identified in the thin film specimen, wherein lateral resolution is about the size of the thickness of the section.

9. A method according to claim 8, and further comprising the steps of milling the semiconductor device with the focused ion beam such that the thin film specimen has a thickness of about 0.1 micrometers.

10. A method according to claim 8, and further comprising the steps of milling the semiconductor device with the focused ion beam such that the thin film specimen has a length of about 20 micrometers and a width of about 5 micrometers.

11. A method according to claim 8, and further comprising the steps of depositing a conductive material using a gallium or other appropriate ion emitted from the focused ion beam.

12. A method according to claim 8, wherein the step of creating the electrical connection points further comprise the steps of:

irradiating gallium or other appropriate ions onto predetermined sections of the thin film specimen by a focused ion beam; and depositing a conductive film onto the irradiated sections using the focused ion beam to create the electrical connection points.

13. A method according to claim 8, and further comprising one of the steps of mounting the thin film specimen on a holder such as a transmission electron microscope grid when creating the electrical connection points or making connection points to part of a wafer after exposing the device using FIB cuts.

14. A method according to claim 8, and further comprising the step of removing the thin film specimen by one of a charged glass or metal tip removal tool.

15. A method of detecting defects within a semiconductor device comprising the steps of:

focusing an ion beam in predetermined directions onto an area of a semiconductor device that is believed to have a suspected defect;

milling a portion of the semiconductor device and forming a thin film specimen that will be removed from the semiconductor device;

removing the thin film specimen from the semiconductor device;

mounting the thin film specimen onto an insulated film mount;

creating electrical connection points on previously unexposed portions of the thin film specimen while the thin film specimen is mounted on the insulated film mount by depositing a line of conductive material using a focused ion beam;

generating a current through at least one electrical connection point;

scanning the surface of the thin film specimen with an electron beam in a scanning electron microscope and observing for contrast; and determining processing errors which can be identified in the thin film specimen, wherein lateral resolution is about the electron beam size.

16. A method according to claim 15, and further comprising the step of depositing a conductive material using a gallium or other appropriate ion emitted from the focused ion beam.

17. A method according to claim 15, and further comprising one of the steps of mounting the thin film specimen on a holder such as a transmission electron microscope grid or mounting on a piece of a wafer when creating the electrical connection points.

18. A method according to claim 15, wherein the step of creating the electrical connection points further comprises the steps of:

irradiating gallium ions onto predetermined sections of the thin film specimen by a focused ion beam; and depositing a conductive film onto the irradiated sections using the focused ion beam to create the electrical connection points.

19. A method according to claim 15, and further comprising the steps of milling the semiconductor device with the focused ion beam such that the thin film specimen has a thickness of about 0.1 micrometers.

20. A method according to claim 15, and further comprising the steps of milling the semiconductor device with the focused ion beam such that the thin film specimen has a length of about 20 micrometers and a width of about 5 micrometers.

21. A method according to claim 15, and further comprising the step of removing the thin film specimen by one of a charged glass or metal tip removal tool.

22. A method of detecting defects within a semiconductor device comprising the steps of:

focusing an ion beam in predetermined directions onto a wafer that is believed to have a suspected defect such that a focused ion beam cuts the area of the semiconductor device to expose an area of interest that is to be analyzed for defects;

creating electrical connection points to the edge of the wafer by depositing a line of conductive material using a focused ion beam;

scanning the surface of the exposed area of interest with an electron beam in a scanning electron microscope;

analyzing internally generated currents as detected by an external amplifier; and determining processing errors which can be identified in the wafer, wherein lateral resolution is about the electron beam size.

* * * * *